United States Patent [19]

Chen

[11] Patent Number: 5,304,648
[45] Date of Patent: Apr. 19, 1994

[54] PYRAZINE PREPARATION

[75] Inventor: Teh-Kuei Chen, Gaylordsville, Conn.

[73] Assignee: Nestec S.A., Vevey, Switzerland

[21] Appl. No.: 953,466

[22] Filed: Sep. 29, 1992

[51] Int. Cl.$^5$ .................. C07D 241/02; C07D 405/06
[52] U.S. Cl. ..................................... 544/410; 544/405
[58] Field of Search ............................... 544/410, 405

[56] References Cited

U.S. PATENT DOCUMENTS

| | | | |
|---|---|---|---|
| 3,925,378 | 12/1975 | Voges et al. | 544/410 |
| 4,046,763 | 9/1977 | Schwartz et al. | 544/410 |
| 4,097,478 | 6/1978 | Sato | 544/410 |
| 4,755,514 | 7/1988 | Ohta | 544/410 |
| 4,788,289 | 11/1988 | Su et al. | 544/410 |
| 4,855,431 | 8/1989 | Chang et al. | 544/410 |

FOREIGN PATENT DOCUMENTS 2294667 12/1987 Japan ..................... 544/410

OTHER PUBLICATIONS

An English Language Disclosure of Yokota, et al., Japanese Kokai 52-97983 (1977).
An English Language Disclosure of Kosuge, et al., Japanese Kokai 52-97983 (1977).
Chiu et al., "Substitution of Pyrazines by Aldehydes in Model Systems", J. Agric. Food Chem., 38, (1990).

*Primary Examiner*—Cecilia Tsang
*Attorney, Agent, or Firm*—Vogt & O'Donnell

[57] ABSTRACT

Pryrazine compounds are obtained by reacting ammonium ions, an aldehyde, and a 1-hydroxy-2-ketone by heating and refluxing an aqueous medium containing the same wherein at least the ketone is introduced dropwise to obtain a reaction medium containing pyrazine compounds, and after which, the pyrazine compounds are isolated from the reaction medium.

11 Claims, No Drawings

PYRAZINE PREPARATION

BACKGROUND OF THE INVENTION

The present invention relates to a process for the preparation of pyrazines, more particularly trialkyl pyrazines which are useful in food applications.

Alkyl pyrazines are important flavour components which are formed during the cooking of many kinds of foods. Generally, they impart roasted or burnt aromas to cooked foods. There is an expectation of an increase in the usage of alkyl pyrazines in the food industry, especially in the booming market of microwaveable foods.

The formation of alkyl pyrazines in foods has been extensively studied using carbohydrate-ammonia model systems. But these types of reactions always give a complex mixture of products with low total yields.

Chiu, et al., J. Agric. Food. Chem. 38, 58–61 (1990) describe an investigation of the effect of long chain aldehydes on the formation of long-chain alkyl-substituted pyrazines in model systems of acetol (hydroxy acetone-a 1-hydroxy-2-ketone) and ammonium acetate (known precursors of pyrazines in food systems) with and without the addition of pentanal or hexanal (well known degradation products of lipids). However, it has been found that the yields of the trialkyl pyrazines are only of the order of about 0.5%.

SUMMARY OF THE INVENTION

It has been found that, in a process for preparing pyrazine compounds similar to the Chiu process noted above, greatly increased yields can be achieved by adding at least the acetol or other 1-hydroxy-2-ketones dropwise to the remainder of the reaction mixture.

Accordingly, the present invention provides a process for the preparation of pyrazine compounds which comprises reacting in an aqueous medium, a 1-hydroxy-2-ketone, ammonium ions which are provided by an ammonium compound, and an aldehyde during which the 1-hydroxy-2-ketone is added dropwise to form an isomeric pair of pyrazine compounds and isolating the pyrazine compounds.

DETAILED DESCRIPTION OF THE INVENTION

In the practice of the present invention, although ammonia gas could be bubbled into water to form the aqueous medium containing the ammonium ions, it is most practical to employ an aqueous solution of an ammonium-containing compound including the ammonium salts of organic and inorganic acids, and other equivalent ammonium-containing compounds. Employment of ammonium salts of weak acids is preferred since it has been found that such act as a buffer agent against formation of acetic acid and hence, buffer the pH, which decreases during the reaction. Such ammonium salts include ammonium acetate, citrate, formate, lactate, oxalate, succinate and tartrate, and diammonium phosphate, etc., individually or in combination.

Other ammonium salts of stronger acids, while not being particularly active may also be employed to effect the reaction, and such include ammonium chloride and sulfate, etc., and when the pyrazine product is to be employed with a food composition, all such ammonium-containing compounds should of course be deemed to be acceptable in processes related to preparing food products.

The 1-hydroxy-2-ketone may contain from 3 to 14 carbon atoms and may be, for instance, acetol.

The aldehyde may contain from 1 to 12 carbon atoms, preferably contains from 2 to 8 carbon atoms and may be, for example, acetaldehyde, methylbutyraldehyde, isobutyraldehyde, propionaldehyde, pentanal, 2-methyl pentanal, hexanal, 3-methyl-mercaptopropionaldehyde, benzaldehyde, phenylacetaldehyde or 2'-furfuraldehyde.

The 1-hydroxy-2-ketone and the ammonium salts are advantageously employed in a molar ratio of about 1:1 to about 1:5, and preferably, about 1:1.5 to about 1:2.5, 1-hydroxy-2-ketone:ammonium salt, and above. Although it also has been found that the higher the amount of ammonium salt, the better the buffering action and the greater the rate of reaction, amounts of ammonium salt higher than the 1:5 ratio, noted above, have not been found to increase yield significantly, and also have been found to generate less than desirable amounts of ammonia gas. Thus, other basic buffering agents may be employed usefully to maintain the reaction mixture weakly acidic, and such has been found to reduce generation of ammonia gas. Such agents may include compounds such as sodium acetate, trisodium phosphate and other alkali salts and the like. Again, if the final product is to be employed in a food application, such agents should be deemed acceptable for use in processes related to preparing food products.

The aldehyde and the ammonium salt are advantageously employed in a molar ratio of from 1:1 to 1:3 and preferably from 1.25 to 2.5.

In general, the pH of the reaction mixture will not fall below a pH of about 4.5 to 5, and the buffering agents may be employed to maintain a pH of above 5.

Although the amount of water employed may vary considerably, generally, as the amount of water is increased, the reaction rate decreases. Thus, although the amount of water present may range from about 0.5 to about 100 parts by weight per part of the total weight of 1-hydroxy-2-ketone, aldehyde and ammonium salt employed, the amount most advantageously employed is merely that amount sufficient to place the ammonium-containing composition, and any pH-adjusting compositions, in solution at the reaction temperatures.

In the practice of the present invention the reactants are conveniently heated and refluxed, e.g., at atmospheric pressure, in any suitable heat-stable vessel, as is known in the reflux art. If desired, the 1-hydroxy-2-ketone may be added dropwise alone to the remainder of the reaction mixture or a mixture containing the 1-hydroxy-2-ketone and ammonium ions may be added dropwise to the aldehyde to form the reaction medium. However, preferably a mixture of the 1-hydroxy-2-ketone and the aldehyde is added dropwise during the reaction to an aqueous medium containing the ammonium ions provided by ammonium compound.

The time of reaction employed is not critical, other than to the extent such impacts upon yield, and such may range up to about 15 hours, and generally from about 2 hours to 8 hours.

After the reaction, the reaction product is contained in the reacted mixture. Isolation of the desired product is effected by increasing the pH of the liquid reacted mixture to an alkaline pH, i.e., above pH of about 7, after which the crude product is separated from the pH-increased liquid by means such as steam distillation, for example, using a modified Likens-Nickerson steam distillation extractor with or without organic solvent, which may be followed by final purification by vacuum distillation. The process of steam distillation in the absence of an organic solvent is highly desirable for products in food applications. Preferably, before isolation of the desired products, the pH is increased to at least about 8, which may be performed under ambient conditions.

Bases which may be employed to increase the pH of the liquid of the reacted mixture are preferably strong bases and include NaOH, KOH and NH$_4$OH, and the like. Such are preferably added in aqueous solution since it is desirable to dilute the reacted mixture with water.

The products of the present invention provide desirable flavorants using known precursors in food systems which may be added to a variety of foodstuffs to impart non-specific or specific roasted notes. Products of the present invention, therefore, are combined advantageously in food compositions.

EXAMPLES

The following Examples further illustrate the present invention.

EXAMPLE 1

Preparation of 2-(2'-methylbutyl)-3,5(6)-dimethylpyrazine

A mixture of 40 g (0.52 moles) ammonium acetate, 30 g of sodium acetate and 60 g of water in a 3-neck 500 ml round bottom flask was heated in an oil bath maintained at 135° C. When the internal temperature reached 105° C., a mixture of 22.7 g (0.276 moles) of 90% acetol and 26.1 g of 2-methylbutyraldehyde (0.318 moles) was added dropwise over a period of 3 hours and refluxed for an additional 20 minutes. 60 g of 20% NaOH solution, were added after the reaction mixture had cooled to room temperature. Using a modified Likens-Nickerson steam distillation extractor, the steam volatile products were extracted with methylene chloride for 5 hours. After removal of the methylene chloride, the crude products were distilled under vacuum. The desired products 2-(2'-methylbutyl)-3,5(6)-dimethylpyrazine (5.02 g 20.4% yield) were collected at 125–132° C. (42 mmHg, uncorrected). GC/MS analysis indicated that the products were a 1 to 1 mixture of 2-(2'-methylbutyl)-3,5-dimethylpyrazine and 2-(2'-methylbutyl)-3,6-dimethylpyrazine.

EXAMPLE 2

Preparation of 2-isobutyl-3,5(6)-dimethylpyrazine

By following a similar procedure to that described in example 1, 5.12 g (22.3% yield) of 2-isobutyl-3,5 (6)-dimethylpyrazine (b.p. 117°–123° C., 57 mmHg, uncorrected) were prepared from the reaction of 23.2 g of 90% acetol (0.28 moles), 22.3 g of isobutyraldehyde (0.33 moles) and 40 g of ammonium acetate/30 g of sodium acetate under the same conditions.

EXAMPLE 3

Preparation of 2-propyl-3,5(6)-dimethylpyrazine

By following a similar procedure to that described in example 1, 4.76 g (21.8 % yield) of 2-propyl-3,5(6)-dimethylpyrazine (b.p. 128°–133° C., 100 mmHg, uncorrected) were prepared from the reaction of 23.2 g of 90% acetol (0.28 moles), 18 g of propionaldehyde (0.31 moles) and 40 g of ammonium acetate/30 g of sodium acetate under the same conditions.

EXAMPLE 4

Preparation of 2-pentyl-3,5(6)-dimethylpyrazine

By following a similar procedure to that described in Example 1, the reaction of 20.5 g of 90% acetol (0.25 moles, 23.8 g of valeraldehyde (0.29 moles), 40 g of ammonium acetate and 30 g of sodium acetate was carried out except that the steam distillation extraction using modified Likens-Nickerson extractor was carried out without using methylene chloride. The steam-distilled oil was separated, dried over anhydrous sodium carbonate and purified by vacuum distillation. The product of 2-pentyl-3,5(6)-dimethylpyrazine was obtained in 17.3% yield (3.92 g, b.p. 130°–136° C., 40 mmHg, uncorrected).

EXAMPLE 5

Preparation of 2-(2-furfuryl)-3,5(6)-dimethylpyrazine

By following a similar procedure to that described in example 1,1.84 g (7.3% yield) of 2-(2-furfuryl)-3,5(6)-dimethylpyrazine (b.p. 148°–155° C., 40 mmHg, uncorrected) were prepared from the reaction of 22.3 g of 90% acetol (0.27 moles), 29.3 g of 2-furfural and 40 g of ammonium acetate/30 g of sodium acetate under the same conditions.

EXAMPLE 6

Preparation of 2-isobutyl-3,5(6)-diethylpyrazine

By following a similar procedure to that described in example 4, using no organic solvent extraction, 7.74 g (20.9 % yield) of 2-isobutyl-3,5(6)-diethylpyrazine were prepared from the reaction of 35.8 g of 95% 1-hydroxy-2-butanone (0.39 moles), 30.6 g of isobutyraldehyde (0.43 moles) and 60 g of ammonium acetate and 30 g of sodium acetate under the same conditions.

EXAMPLE 7

Preparation of 2-(2'-methyl)amyl-3,5(6)-dimethylpyrazine

By following a similar procedure to that described in example 1, 4.8 g (18.6% yield) of 2-(2'-methyl)amyl-3,5(6)-dimethylpyrazine (b.p. 127°–132° C., 30 mm Hg, uncorrected) were prepared from the reaction of 22.5 g of 90% acetol (0.27 moles), 30 g of 2-methylvaleraldehyde (0.3 moles) and 40 g of ammonium acetate, 30 g of sodium acetate under the same conditions.

I claim:

1. A process for obtaining pyrazine compounds comprising heating and refluxing an aqueous medium containing ammonium ions, an aldehyde and a 1-hydroxy-2-ketone wherein the ketone is introduced into the refluxing aqueous medium dropwise for reacting the ketone with the ammonium ions and aldehyde to obtain a reaction medium containing pyrazine compounds and then isolating the compounds from the reaction medium.

2. A process according to claim 1 wherein the aqueous medium contains the ammonium ions and wherein the ketone and aldehyde are added dropwise to the refluxing medium.

3. A process according to claim 1 wherein the aqueous medium contains the aldehyde and wherein the ketone and ammonium ions are added dropwise to the refluxing medium.

4. A process according to claim 1 wherein the pH of the reaction medium is increased to an alkaline pH and then steam distilled for isolating the compounds.

5. A process according to claim 4 wherein the pH of the reaction medium is increased to at least about 8.

6. A process according to claim 4 further comprising vacuum distilling the steam distilled compounds to purify the trialkyl compounds.

7. A process according to claim 1 wherein the ammonium ions are provided by an ammonium salt of a weak acid.

8. A process according to claim 7 wherein the ammonium salt is selected from the group consisting of ammonium acetate, citrate, formate, lactate, oxalate, succinate, tartrate and diammonium phosphate.

9. A process according to claim 1 wherein the ketone is acetol.

10. A process according to claim 1 wherein the aldehyde is selected from the group consisting of acetaldehyde, methylbutyraldehyde, isobutyraldehyde, propionaldehyde, pentanal, 2-methyl pentanal, hexanal, 3-methylmercaptopropionaldehyde, benzaldehyde, phenylacetaldehyde or 2'-furfuraldehyde.

11. A process according to claim 1 wherein the ketone is acetol, the aldehyde is selected from the group consisting of acetaldehyde, methylbutyraldehyde, isobutyraldehyde, propionaldehyde, pentanal, 2-methyl pentanal, hexanal, 3-methyl-mercaptopropionaldehyde, benzaldehyde, phenylacetaldehyde or 2'-furfuraldehyde and the ammonium ions are provided by an ammonium salt of a weak acid.

* * * * *